(12) United States Patent
Hauer et al.

(10) Patent No.: US 8,198,069 B2
(45) Date of Patent: Jun. 12, 2012

(54) METHOD OF PRODUCING AN OPTICALLY ENRICHED TERTIARY ALCOHOL FROM AN EPOXIDE USING HALOHYDRIN DEHALOGENASE

(75) Inventors: Bernhard Hauer, Fussgönheim (DE); Dick B. Janssen, Groningen (NL); Maja Majeric-Elenkov, Zagreb (HR)

(73) Assignee: BASF SE (DE)

( * ) Notice: Subject to any disclaimer, the term of this patent is extended or adjusted under 35 U.S.C. 154(b) by 875 days.

(21) Appl. No.: 12/158,334

(22) PCT Filed: Dec. 13, 2006

(86) PCT No.: PCT/EP2006/069626
§ 371 (c)(1),
(2), (4) Date: Jun. 20, 2008

(87) PCT Pub. No.: WO2007/071599
PCT Pub. Date: Jun. 28, 2007

(65) Prior Publication Data
US 2008/0299626 A1 Dec. 4, 2008

(30) Foreign Application Priority Data
Dec. 21, 2005 (EP) .................................... 05112657

(51) Int. Cl.
*C12P 41/00* (2006.01)
*C12P 7/02* (2006.01)
(52) U.S. Cl. ........................................ 435/280; 435/155
(58) Field of Classification Search .................. None
See application file for complete search history.

(56) References Cited

U.S. PATENT DOCUMENTS 7,993,904 B2 * 8/2011 Hauer et al. .................. 435/280
2003/0124693 A1 7/2003 Spelberg et al.

FOREIGN PATENT DOCUMENTS

| JP | 05-317066 A | 12/1993 |
| WO | WO-98/53081 A1 | 11/1998 |
| WO | WO-2005/017141 A1 | 2/2005 |
| WO | WO 2005/018579 A2 | 3/2005 |

OTHER PUBLICATIONS

Lebel et al., "Chromium catalyzed kinetic resolution of 2,2-disubstituted epoxides", Tetrahedron Letters 40 : 7303-7306 (1999).*
Hasnaoui, G. et al., "Nitrite-mediated hydrolysis of epoxides catalyzed by halohydrin dehalogenase from *Agrobacterium radiobocterium* AD1: a new tool for the kinetic resolution of epoxides," Tretrahedron Assyrnetry, 2005, vol. 16, pp. 1685-1692.
Chen, S.-T. et al., "Preparation of optically active tertiary alcohols by enzymatic methods. Application to the synthesis of drugs and natural products," Journal of Organic Chemistry, 1997, vol. 62, pp. 4349-4357.
van Hylckama Vlieg, J.T. et al., "Halohydrin dehalogenases are structurally and mechanistically related to short-chain dehydrogenases/reductases," Journal of Bacteriology, 2001, vol. 183, No. 17, pp. 5058-5066.
Lutje Spelberg, J.H. et al., "Exploration of the biocatalytic potential of a halohydrin dehalogenase using chromogenic substrates," Tetrahedron Assymetry, 2002, vol. 13, pp. 1083-1089.
Elenkov, M.M., et al., "Enantioselective ring opening of epoxides with cyanide catalysed by halohydrin dehalogenases; A new approach to non-racemic β-Hydroxy nitriles," Advanced Synthesis & Catalysis, 2006, vol. 348, pp. 579-585.
Nakamura, T. et al., "A new enzymatic synthesis of (R)-γ-chloro-β-hydroxybutyronitrile,"Tetrahedron, 1994, vol. 50, No. 41, pp. 11821-11826.
Lutje Spelberg, J.H. et al., "Highly enantioselective and regioselective biocatalytic azidolysis of aromatic epoxides," Organic Letters, 2001, vol. 3, No. 1, pp. 41-43.
Nakamura, T. et al., "A new catalytic function of halohydrin hydrogen-halide-lyase, synthesis of β-hydroxynitriles from epoxides and cyanide," Biochemical and Biophysical Research Communications, 1991, vol. 180, No. 1, pp. 124-130.
Mosset, P. et al., "Trimethylsuifonium methylsulfate, a simple and efficient epoxidizing agent," Synthetic Communications., 1985, vol. 15, No. 8, pp. 749-757.
Schwartz, N.N., et al., "Epoxidations with *m*-chloroperbenzoic acid," Journal of Organic Chemistry, 1964, vol. 29, pp. 1976-1979.

* cited by examiner

*Primary Examiner* — Sandra Saucier
(74) *Attorney, Agent, or Firm* — Connolly Bove Lodge & Hutz LLP

(57) ABSTRACT

A process for the production of an optically enriched tertiary alcohol of the formula (2a) or (2b), by reacting an epoxide of the formula (1) with a nucleophilic agent Nu in the presence of halohydrin dehalogenase.

10 Claims, No Drawings

METHOD OF PRODUCING AN OPTICALLY ENRICHED TERTIARY ALCOHOL FROM AN EPOXIDE USING HALOHYDRIN DEHALOGENASE

RELATED APPLICATIONS

This application is a national stage application under 35 U.S.C. §371 of PCT/EP2006/069626, filed Dec. 13, 2006, and claims priority of European application 05112657.1, filed Dec. 21, 2005.

SEQUENCE LISTING SUBMISSION

The Sequence Listing associated with this application is filed in electronic format via EFS-Web and hereby incorporated by reference in its entirety into the specification. The name of the text file containing the Sequence Listing is SequenceList__12810__00702_US. The size of the text file is 9 KB, and the text file was created on Jun. 10, 2008.

FIELD OF THE INVENTION

The invention relates to a process for the production of an optically enriched tertiary alcohol.

BACKGROUND OF THE INVENTION

Nakamura et al. (Tetrahedron 1994, Vol. 50, No 41, 11821-11826) describe an enzymatic synthesis of (R)-γ-chloro-β-hydroxybutyronitrile by *Corynebacterium* halohydrin hydrogen-halide lyase.

Lutje Spelberg et al. (Org. Letters 2001, Vol. 3, No. 1, 41-43) describe the enantioselective and regioselective biocatalytic azidolysis of aromatic epoxides.

Nakamura et al. (Biochem. Biophys. Res. Comm. 1991, Vol 180, No. 1, 124-130) describe a new catalytic function of halohydrin hydrogen-halide-Lyase for the synthesis of β-hydroxynitriles.

Spelberg et al. (Tetrahedron Asymmetry 2002, 13, 1083-1089) analyze the biocatalytic potential of a halohydrin dehalogenase from *Agrobacterium radiobacter*.

WO 2005/017141 disclose improved halohydrin dehalogenases and related polynucleotides.

US 2003/0124693 A1 disclose the enzymatic conversion of epoxides.

None of the prior art disclose the production of tertiary alcohols.

DETAILED DESCRIPTION OF THE INVENTION

The present invention provides a process for the production of an optically enriched tertiary alcohol of the formula (2a) or (2b), by reacting an epoxide of the formula (1) with a nucleophilic agent Nu in the presence of halohydrin dehalogenase

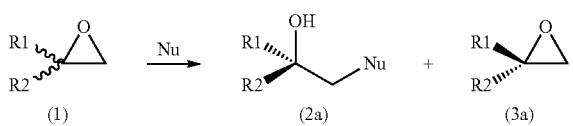

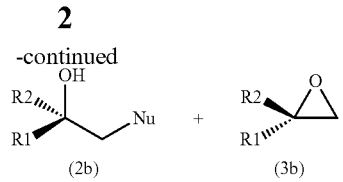

wherein R1 and R2 are chosen independent from each other from optionally substituted alkyl groups, aryl groups, aralkyl groups, alkenyl groups, cycloalkyl groups and Nu is chosen from the group of cyanide ($CN^-$), azide ($N_3^-$), nitrite ($NO_2^-$), nitrate ($NO_3^-$), cyanate ($OCN^-$), thiocyanate ($SCN^-$), chloride ($Cl^-$), bromide ($Br^-$), iodide ($I^-$), formate ($HCOO^-$), and recovering the optically enriched alcohol.

The enzyme used is a halohydrin dehalogenase. A highly suitable halohydrin dehalogenase is a polypeptide having an amino acid sequence as shown in the Sequence Listing (SEQ ID NO: 1 to NO:4) or a homologue or functional derivative thereof. In the context of the invention, the term 'a homologue' refers to a sequence which is at least for 90% homologous, and preferably at least 90% identical, to the sequence of which it is a homologue. A functional derivative is a polypeptide which has undergone a minor derivatization or modification substantially without adversely affecting the enzymatic and catalytic properties of the polypeptide. Suitable examples of enzymes that can be used are halohydrin dehalogenase of *Agrobacterium radiobacter* (CBS 750.97), *Mycobacterium* sp. strain GP1 (Poelarends et al J. Bacteriol., 1999, 181, 2050) or *Arthrobacter* sp. strain AD2 (van den Wijngaard et al., J. Bacteriol., 1991, 124).

Particular good results have been obtained using a halohydrin dehalogenase derived from *Agrobacterium radiobacter* strain AD1 deposited at the Centraal Bureau voor de Schimmelcultures on May 7, 1997 under deposit number CBS 750.97. Another enzyme obtained from this organism has been described extensively in the international patent application WO 98/53081 for its epoxide hydrolase activity.

It is to be noted that an enzyme used according to the invention, a halohydrin dehalogenase, should be distinguished from epoxide hydrolases. The latter have been described extensively in Archer, Tetrahedron, 53 (1997), pp. 15617-15662. The only feature that both types of enzymes may have in common is that they can be isolated from *Agrobacterium* radiobacter strain AD1. Likewise, Lutje Spelberg et al., Tetrahedron: Asymmetry, 9 (1998), pp. 459-466 and European patent application EP 0 879 890 relate to applications of an epoxide hydrolase.

The activity under process conditions, stability, and enantioselectivity of the halohydrin dehalogenase can be improved by methods known in the field, including site-directed mutagenesis to remove labile groups and to modify the enantioselectivity, directed evolution employing gene shuffling, site-saturation mutagenesis, or structure-inspired random mutagenesis, or error prone PCR. These methods are known in the field (Powell et al., 2001, ACIE 40, 3948; Otten and Quax, 2005, Biomol. Eng. 22, 1; Williams et al., 2004, Cell Mol Life Sci 61:3034). Such mutagenesis methods are applicable for improving halohydrin dehalogenase performance as was recently shown by the construction of mutants with increased activity and enantioselectivity (Tang et al., 2005, Biochemistry 44, 6609; Tang et al., 2003, Biochemistry 42, 14057) and of mutants with improved stability (Tang et al., 2002, Enz Microb Techn. 30, 251).

Improved halohydrin dehalogenases are disclosed eg. in WO 2005/018579 A2 and WO 2005/017141 A1.). The mutations that were introduced include replacements of Cys by Ser.

The enzyme can be added as whole cells, in lyophilized form as a crude extract or as a purified enzyme. The enzyme can be immobilized on a macroscopic carriers such as cellulose, sephadex or dextran. The enzyme can also be applied as crosslinked enzyme crystals (CLEC's) crosslinked enzyme aggregates (CLEAs) (Cao L., F. van Rantwijk, R. A. Sheldon (2000). Cross-linked enzyme aggregates: a simple and effective method for the immobilization of penicillin acylase, in Organic Letters, 2, p. 1361-1364) or entrapped in reversed micelles. In a typical experiment, an enzyme solution is mixed with a buffer solution containing a nucleophile and an epoxide. Optionally, additives such as mercapto ethanol or glycerol can be added to the reaction mixture to stabilize the enzyme.

The epoxide of the formula (1) can be prepared from corresponding ketone using sulfonium ylids, (Mosset, P.; Gree, R. *Syn. Comm.* 1985, 15, 749-757) or by oxidation of alkenes using peroxy-carboxylic acid such as m-CPBA (meta-chloroperoxybenzoic acid). (Schwartz, N. N.; Blumbergs, J. H. *J. Org. Chem.* 1964, 29, 1976-1979).

The R1 and R2 groups are independent from each other optionally substituted, aromatic or aliphatic groups, which preferably contains from 1 to 20, more preferred from 1 to 10 carbon atoms. Preferably, R1 and R2 are chosen from the group of optionally substituted alkyl, aryl, aralkyl, alkenyl, cycloalkyl, and alkoxy groups. An optically enriches tertiary alcohol of the formula (2a) or (2b) can be produced by the process according to the invention only if R1 is chemically distinct from R2.

Preferred examples of the alkyl group represented by R1 or R2 include straight or branched alkyl groups having 1 to 15 carbon atoms such as a methyl group, ethyl group, propyl group, isopropyl group, butyl group, pentyl group, hexyl group, heptyl group or dodecyl group.

Further preferred residues are those where R1 and R2 are chosen from the group H, $—(CH_2)_n—CH_3$, with n=0 to n=8, $—C_6H_5$ (phenyl), $—(CH_2)_n—(C_6H)_5$ (arylalkyl) $—C_6H_{11}$ (cyclohexyl), $CH_2CO_2R^3$ and R3 is chosen from $—CH_3$ (methyl), $—C_2H_5$ (-ethyl), $—C(CH_3)_3$ (tert-butyl).

The alkyl group can have substituents such as a halogen atom, The alkyl group can have a substituent such as an hydroxyl group, for example glycidol. The alkyl group can have a unsubstituted or substituted amino group such as amino, methylamino or dimethylamino. Examples of aryl groups represented by R1 or R2 include phenyl and naphtyl groups. Styrene oxide derivatives having a substituent or multiple substituents on the aromatic ring are examples of the phenyl group. Representative examples of epoxides are styrene oxide, 4-nitrostyrene oxide, 2-nitrostyrene oxide, 3-nitrostyrene oxide, 3-chlorostyrene oxide, 4 chlorostyrene oxide or 2,3-dichlorostyrene oxide. Examples of aralkyl groups represented by R1 or R2 include a benzyl group, 2-phenylethyl group and a 1-naphtylmethyl group. Examples of alkenyl groups represented by R1 or R2 include a vinyl group, allyl group and 5-hexenyl group. Examples of cycloalkyl groups represented by R1 or R2 include a cyclopropyl group, cyclobutyl group, cyclopentyl group and cyclohexyl group. Examples of alkoxy groups represented by R1 or R2 include a phenoxy group, 4-nitrophenoxy group, napthyloxy group, methoxy group, hexyloxy group and vinyloxy group.

The epoxide (1) can be present in solubilized form in a concentration of 1 to 300 mM or as a second solid or liquid phase in concentration up to 300 mM in the reaction medium. The epoxide itself can be the second phase or it can be dissolved in a second organic phase. This can be done by dissolving the epoxide in an organic solvent which is immiscible with water, such as hexane or octane. The obtained solution is then brought into contact with the aqueous phase containing the enzyme and the two phases are vigorously mixed. The use of such a second phase has the advantage that the separation of the epoxide and the alcohol after the reaction can be simplified. Generally, the alcohol is expected to remain solubilized in the aqueous phase and the epoxide can typically be recovered from the organic phase. Preferably, the epoxide is prior to its conversion brought in an aqueous medium in which it will preferably be present in an amount of 0.01 to 20 wt. %, based on the combined weights of the aqueous medium and the epoxide.

It is preferred that the reaction is carried out in a buffered aqueous medium to which the epoxide (1) is solubilized or is added as a second solid or liquid phase. Suitable buffers are for example Tris-buffer (2 amino-2-(hydroxymethyl)-1,3 propanediol adjusted to a desired pH with $H_2SO_4$), glycine-buffer (glycine adjusted to a desired pH by NaOH), phosphates buffer or MOPS buffer (4-morpholinepropanesulfonic acid adjusted to a desired pH with NaOH). These are preferably used a concentration of 50 to 250 mM.

Optionally, co-solvents like dimethyl sulfoxide, tetrahydrofuran or acetonitrile may be added to increase the solubility of the epoxide (1). Co-solvents may be added in amounts of 5 vol. % up to 50 vol. %. An increasing percentage of co-solvent may favor the solubility of the epoxide (1). However, a disadvantageous inactivation of the enzyme can be observed at higher co-solvent concentrations.

The pH of the medium preferably lies between 3 and 12, more preferably between 6.5 and 8. The temperature at which the reaction is carried out preferably lies between 0 to 60° C., more preferably between 20 and 30° C.

The nucleophilic agent Nu reacting in the process according to the invention is chosen from cyanide ($CN^-$), azide ($N_3^-$), nitrite ($NO_2^-$), nitrate ($NO_3^-$), cyanate ($OCN^-$), thiocyanate ($SCN^-$), chloride ($Cl^-$), bromide ($Br^-$), iodide ($I^-$), formate ($HCOO^-$).

The epoxide (1) can be added at once, fed-batch-wise or continuously to the reaction. Preferred is a fed-batch-wise or continuous addition in order to suppress the conversion of the epoxide (3a) and (3b) respectively.

After the reaction the whole reaction mixture can be extracted using organic solvents such as diethylether, ethyl acetate, dichloromethane or toluene. The epoxide enantiomer (3a) or (3b) and the optically enriched tertiary alcohol of the formula (2a) or (2b) can subsequently be separated by techniques such as crystallisation (in the case of solid substances), fraction distillation or flash chromatography e.g. on silica 60H using heptane/ethylacetate(ratio 7:3) as eluent or other separation techniques well-known in the art.

The enantiomeric composition of the epoxides (3a) or (3b) and alcohols (2a) or (2b) can be determined using chiral gaschromatography or chiral HPLC.

The separated optically enriched epoxides (3a) or (3b) can be used for further synthetic steps, especially for a ring-opening with an alternative nucleophilic agent such as $NO_2$ which allows the production of a substituted tertiary alcohol in an optically pure form.

The invention will now be further elucidated by the following, non-restrictive examples.

EXAMPLES

Example I 500 mg (5.8 mmol) of racemic 2-ethyl-2-methyloxirane was dissolved in 100 mL Tris-$SO_4$ buffer (200 mM, pH 7.5), followed by addition of purified enzyme (15 mg of halohydrin dehalogenase HheC in 450 μL buffer) and 189 mg (2.9 mmol) NaN$_3$. The reaction mixture was stirred at room temperature (24° C.) and monitored by gas chromatography (GC). The reaction was stopped after 1 h and extracted three times by adding 50 mL ethylacetate. The combined organic phases were dried over Na$_2$SO$_4$ and evaporated. The crude product was chromatographed on a silica gel 60 H using pentane/CH$_2$Cl$_2$ (4:6) as eluent. This yielded pure (S)-2-ethyl-2-methyloxirane (205 mg, 41% yield, e.e.>99%) and (R)-azido-2-methylbutan-2-ol (320 mg, 43% yield, e.e.>99%). Optical purities were determined by GC using a Chiraldex G-TA column (30 m×0.25 mm×0.25 μm). The NMR data were identical with those of synthesized racemic reference compounds.

Example II 300 mg (2.14 mmol) of racemic 2-cyclohexyl-2-methyloxirane was dissolved in 40 mL Tris-SO$_4$ buffer (200 mM, pH 7.5), followed by addition of purified enzyme (9 mg of halohydrin dehalogenase HheC in 280 μL buffer) and 69 mg (1.06 mmol) of NaN$_3$. The reaction mixture was stirred at room temperature (24° C.) and monitored by gas chromatography (GC). The reaction was stopped after 2.5 h and extracted with 3×25 mL of ethylacetate. The combined organic phase was dried over Na$_2$SO$_4$ and solvent was evaporated. The crude product was chromatographed on a silica gel 60 H using pentane/CH$_2$Cl$_2$ (4:6) as eluent, which yielded pure (S)-2-cyclohexyl-2-methyloxirane (155 mg, 51% yield, e.e. 76%) and (R)-azido-2-cyclohexylpropanol-2-ol (163 mg, 41% yield, e.e.>99%). Optical purities were determined by GC using a Chiraldex G-TA column (30 m×0.25 mm×0.25 μm). The NMR data were identical with those of synthesized racemic reference compounds.

Example III 200 mg (1.42 mmol) of racemic 2-cyclohexyl-2-methyloxirane was dissolved in 25 mL Tris-SO$_4$ buffer (200 mM, pH 7.5), followed by addition of purified enzyme (9 mg of halohydrin dehalogenase HheC in 1.2 ml buffer) and 35 mg (0.71 mmol) NaCN. The reaction mixture was stirred at room temperature (24° C.) and monitored by gas chromatography (GC). The reaction was stopped after 24 h and extracted three times with 15 mL ethylacetate. The combined organic phases were dried over Na$_2$SO$_4$ and the solvent was evaporated. The crude product was chromatographed on a silica gel 60 H using pentane/CH$_2$Cl$_2$ (4:6) as eluent, which yielded pure (S)-2-cyclohexyl-2-methyloxirane (105 mg, 52% yield, e.e. 71%) and (S)-3-cyclohexyl-3-butanenitrile (95 mg, 40% yield, e.e. 100%). Optical purities were determined by GC using a Chiraldex G-TA column (30 m×0.25 mm×0.25 μm). The NMR data were identical with those of synthesized racemic reference compounds.

Example IV 200 mg (1.53 mmol) of racemic methyl 2-methyloxiraneacetate was dissolved in 30 mL Tris-SO$_4$ buffer (200 mM, pH 7.5), followed by addition of purified enzyme (15 mg of halohydrin dehalogenase HheC in 450 ρL buffer) and 38 mg (0.77 mmol) NaCN. The reaction mixture was stirred at room temperature (22° C.) and monitored by gas chromatography (GC). The reaction was stopped after 2 h and extracted 3×25 mL ethylacetate. The organic phase was dried over Na$_2$SO$_4$ and evaporated. The crude product was chromatographed on a silica gel 60 H column using pentane/CH$_2$Cl$_2$ (4:6) as eluent. This yielded pure (S)-methyl 2-methyloxiraneacetate (75 mg, 37% yield, e.e. 81%) and (S)-methyl 4-cyano-3-hydroxy-3-methylbutanoate (84 mg, 35% yield, e.e.>99%). The optical purities were determined by GC using a Chiraldex G-TA column (30 m×0.25 mm×0.25 μm). The NMR data were identical with those of synthesized racemic reference compounds.

---

The invention claimed is:

1. A process for the production of an optically enriched tertiary alcohol of formula (2a) or (2b), comprising reacting an epoxide of formula (1) with a nucleophilic agent Nu catalyzed by halohydrin dehalogenase

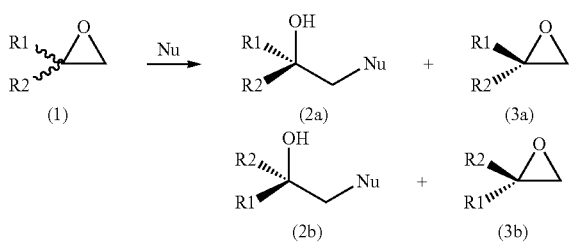

wherein R1 and R2 are chemically distinct and are independently selected from the group consisting of straight or branched alkyl groups having 1 to 15 carbon atoms and optionally substituted aryl groups, arylalkyl groups, alkenyl groups and cycloalkyl groups, and wherein Nu is selected from the group consisting of $CN^-$, $N_3^{31}$, $NO_2^-$, $NO_3^-$, $SCN^-$, $Cl^-$, $Br^-$, $I^-$, or $HCOO^-$;

and recovering the optically enriched alcohol.

2. The process of claim 1, wherein R1 and R2 independently are $-(CH_2)_n-CH_3$, wherein n is 0 to 8; $-C_6H_5$; $-(CH_2)_n-(C_6H)_5$; $-C_6H_{11}$; or $CH_2CO_2R3$, wherein R3 is $-CH_3$, $-C_2H_5$, or $-C(CH_3)_3$.

3. The process of claim 1, wherein the halohydrin dehalogenase is a polypeptide comprising the amino acid sequence of SEQ ID NOs: 1, 2, 3 or 4.

4. The process of claim 2, wherein the halohydrin dehalogenase is a polypeptide comprising the amino acid sequence of SEQ ID NOs: 1, 2, 3 or 4.

5. The process of claim 1, further comprising reacting the epoxide of formula (1) with the nucleophilic agent Nu in the presence of halohydrin dehalogenase at a temperature of 0° C. and 60° C.

6. The process of claim 2, further comprising reacting the epoxide of formula (1) with the nucleophilic agent Nu in the presence of halohydrin dehalogenase at a temperature of 0° C. and 60° C.

7. The process of claim 1, further comprising separating the optically enriched tertiary alcohol (2a) or (2b) from the epoxide (3a) or (3b) by crystallization.

8. The process of claim 2, further comprising separating the optically enriched tertiary alcohol (2a) or (2b) from the epoxide (3a) or (3b) by crystallization.

9. The process of claim 1, further comprising a subsequent step comprising reacting at least one of the epoxides (3a) or (3b) with a nucleophilic agent to the corresponding alcohol.

10. The process of claim 2, further comprising a subsequent step comprising reacting at least one of the epoxides (3a) or (3b) with a nucleophilic agent to the corresponding alcohol.

* * * * *

UNITED STATES PATENT AND TRADEMARK OFFICE
CERTIFICATE OF CORRECTION

PATENT NO.        : 8,198,069 B2                                             Page 1 of 1
APPLICATION NO.   : 12/158334
DATED             : June 12, 2012
INVENTOR(S)       : Bernhard Hauer et al.

It is certified that error appears in the above-identified patent and that said Letters Patent is hereby corrected as shown below:

In Claim 1, in column 11, on line 51, "selected from the group consisting of $CN^-$, $N_3^{31}$, $NO_2^-$," should read -- selected from the group consisting of -- $CN^-$, $N_3^-$, $NO_2^-$, --

In Claim 5, in column 12, on line 37, "presence of halohydrin dehalogenase at a temperature of 0°C." should read -- presence of halohydrin dehalogenase at a temperature of 0°C --

In Claim 6, in column 12, on line 41, "presence of halohydrin dehalogenase at a temperature of 0°C." should read -- presence of halohydrin dehalogenase at a temperature of 0°C --

Signed and Sealed this
Fourteenth Day of August, 2012

David J. Kappos
*Director of the United States Patent and Trademark Office*

SEQUENCE LISTING

```
<160> NUMBER OF SEQ ID NOS: 4

<210> SEQ ID NO 1
<211> LENGTH: 254
<212> TYPE: PRT
<213> ORGANISM: Agrobacterium tumefaciens

<400> SEQUENCE: 1

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys Gln Lys Asp Glu Leu Glu Ala Phe Ala Glu Thr Tyr
            35                  40                  45

Pro Gln Leu Lys Pro Met Ser Glu Gln Glu Pro Ala Glu Leu Ile Glu
        50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110
```

```
Asn Ala Val Ala Ser Gln Met Lys Lys Arg Lys Ser Gly His Ile Ile
            115                 120                 125

Phe Ile Thr Ser Ala Thr Pro Phe Gly Pro Trp Lys Glu Leu Ser Thr
        130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250

<210> SEQ ID NO 2
<211> LENGTH: 244
<212> TYPE: PRT
<213> ORGANISM: Arthrobacter agilis

<400> SEQUENCE: 2

Met Val Ile Ala Leu Val Thr His Ala Arg His Phe Ala Gly Pro Ala
1               5                   10                  15

Ala Val Glu Ala Leu Thr Gln Asp Gly Tyr Thr Val Val Cys His Asp
                20                  25                  30

Ala Ser Phe Ala Asp Ala Ala Glu Arg Gln Arg Phe Glu Ser Glu Asn
            35                  40                  45

Pro Gly Thr Ile Ala Leu Ala Glu Gln Lys Pro Glu Arg Leu Val Asp
        50                  55                  60

Ala Thr Leu Gln His Gly Glu Ala Ile Asp Thr Ile Val Ser Asn Asp
65                  70                  75                  80

Tyr Ile Pro Arg Pro Met Asn Arg Leu Pro Leu Glu Gly Thr Ser Glu
                85                  90                  95

Ala Asp Ile Arg Gln Met Phe Glu Ala Leu Ser Ile Phe Pro Ile Leu
                100                 105                 110

Leu Leu Gln Ser Ala Ile Ala Pro Leu Arg Ala Ala Gly Gly Ala Ser
            115                 120                 125

Val Ile Phe Ile Thr Ser Ser Val Gly Lys Lys Pro Leu Ala Tyr Asn
        130                 135                 140

Pro Leu Tyr Gly Pro Ala Arg Ala Ala Thr Val Ala Leu Val Glu Ser
145                 150                 155                 160

Ala Ala Lys Thr Leu Ser Arg Asp Gly Ile Leu Leu Tyr Ala Ile Gly
                165                 170                 175

Pro Asn Phe Phe Asn Asn Pro Thr Tyr Phe Pro Thr Ser Asp Trp Glu
            180                 185                 190

Asn Asn Pro Glu Leu Arg Glu Arg Val Asp Arg Asp Val Pro Leu Gly
        195                 200                 205

Arg Leu Gly Arg Pro Asp Glu Met Gly Ala Leu Ile Thr Phe Leu Ala
210                 215                 220

Ser Arg Arg Ala Ala Pro Ile Val Gly Gln Phe Ala Phe Thr Gly
225                 230                 235                 240
```

Gly Tyr Leu Pro

<210> SEQ ID NO 3
<211> LENGTH: 235
<212> TYPE: PRT
<213> ORGANISM: Mycobacterium sp.

<400> SEQUENCE: 3

```
Met Ala Asn Gly Arg Lys Arg Glu Met Ala Asn Gly Arg Leu Ala Gly
1               5                   10                  15

Lys Arg Val Leu Leu Thr Asn Ala Asp Ala Tyr Met Gly Glu Ala Thr
            20                  25                  30

Val Gln Val Phe Glu Glu Gly Ala Glu Val Phe Ala Asp His Thr
            35                  40                  45

Asp Leu Thr Lys Val Gly Ala Ala Glu Glu Val Val Glu Arg Ala Gly
        50                  55                  60

His Ile Asp Val Leu Val Ala Asn Phe Ala Val Asp Ala His Phe Gly
65                  70                  75                  80

Val Thr Val Leu Glu Thr Asp Glu Glu Leu Trp Gln Thr Ala Tyr Glu
                85                  90                  95

Thr Ile Val His Pro Leu His Arg Ile Cys Arg Ala Val Leu Pro Gln
                100                 105                 110

Phe Tyr Glu Arg Asn Lys Gly Lys Ile Val Val Tyr Gly Ser Ala Thr
            115                 120                 125

Ala Met Arg Cys His Glu Gly Ala Leu Ala Tyr Ser Thr Ala Arg Phe
130                 135                 140

Ala Gln Arg Gly Tyr Val Thr Ala Leu Gly Pro Glu Ala Ala Arg His
145                 150                 155                 160

Asn Val Asn Val Asn Phe Ile Ala Gln His Trp Thr Gln Asn Lys Glu
                165                 170                 175

Tyr Phe Trp Pro Glu Arg Ile Ala Thr Asp Glu Phe Lys Glu Asp Met
            180                 185                 190

Ala Arg Arg Val Pro Leu Gly Arg Leu Ala Thr Ala Arg Glu Asp Ala
        195                 200                 205

Leu Leu Ala Leu Phe Leu Ala Ser Asp Glu Ser Asp Phe Ile Val Gly
    210                 215                 220

Lys Ser Ile Glu Phe Asp Gly Gly Trp Ala Thr
225                 230                 235
```

<210> SEQ ID NO 4
<211> LENGTH: 244
<212> TYPE: PRT
<213> ORGANISM: Corynebacterium sp.

<400> SEQUENCE: 4

```
Met Lys Ile Ala Leu Val Thr His Ala Arg His Phe Ala Gly Pro Ala
1               5                   10                  15

Ala Val Glu Ala Leu Thr Arg Asp Gly Tyr Thr Val Val Cys His Asp
            20                  25                  30

Ala Thr Phe Ala Asp Ala Ala Glu Arg Gln Arg Phe Glu Ser Glu Asn
        35                  40                  45

Pro Gly Thr Val Ala Leu Ala Glu Gln Lys Pro Glu Arg Leu Val Asp
    50                  55                  60

Ala Thr Leu Gln His Gly Glu Ala Ile Asp Thr Ile Val Ser Asn Asp
65                  70                  75                  80

Tyr Ile Pro Arg Pro Met Asn Arg Leu Pro Ile Glu Gly Thr Ser Glu
```

```
                    85                      90                      95

Ala Asp Ile Arg Gln Val Phe Glu Ala Leu Ser Ile Phe Pro Ile Leu
                100                     105                     110

Leu Leu Gln Ser Ala Ile Ala Pro Leu Arg Ala Ala Gly Gly Ala Ser
                115                     120                     125

Val Ile Phe Ile Thr Ser Ser Val Gly Lys Lys Pro Leu Ala Tyr Asn
                130                     135                     140

Pro Leu Tyr Gly Pro Ala Arg Ala Ala Thr Val Ala Leu Val Glu Ser
145                     150                     155                     160

Ala Ala Lys Thr Leu Ser Arg Asp Gly Ile Leu Leu Tyr Ala Ile Gly
                165                     170                     175

Pro Asn Phe Phe Asn Asn Pro Thr Tyr Phe Pro Thr Ser Asp Trp Glu
                180                     185                     190

Asn Asn Pro Glu Leu Arg Glu Arg Val Glu Arg Asp Val Pro Leu Gly
                195                     200                     205

Arg Leu Gly Arg Pro Asp Glu Met Gly Ala Leu Ile Thr Phe Leu Ala
                210                     215                     220

Ser Arg Arg Ala Ala Pro Ile Val Gly Gln Phe Phe Ala Phe Thr Gly
225                     230                     235                     240

Gly Tyr Leu Pro
```